United States Patent [19]

Ketchum et al.

[11] 4,236,404
[45] Dec. 2, 1980

[54] DEVICE FOR MONITORING DISSOLVED GASES IN ELECTRICAL INSULATING LIQUIDS SUCH AS TRANSFORMER OILS

[75] Inventors: Marshall D. Ketchum; Alexander J. Yerman, both of Scotia, N.Y.

[73] Assignee: General Electric Company

[21] Appl. No.: 719,339

[22] Filed: Aug. 31, 1976

[51] Int. Cl.³ .......................................... G01N 31/00
[52] U.S. Cl. .......................................... 73/19; 73/23.1
[58] Field of Search .............................. 73/19, 23, 23.1

[56] References Cited

U.S. PATENT DOCUMENTS

| | | | |
|---|---|---|---|
| 2,846,121 | 8/1958 | Ronnebeck | 73/23.1 |
| 3,247,702 | 4/1966 | Houser et al. | 73/23.1 |
| 3,394,582 | 7/1968 | Munro et al. | 73/23.1 |
| 3,680,359 | 8/1972 | Lynch | 73/23 |
| 3,824,838 | 7/1974 | Ohtsu et al. | 73/23.1 |
| 3,844,160 | 10/1974 | Yamaoka | 73/19 |
| 3,866,460 | 2/1975 | Pearce | 73/19 |
| 3,968,678 | 7/1976 | Krener et al. | 73/19 |

OTHER PUBLICATIONS

Yerman et al., *Instruction Book for GETOM-General Electric Transformer Oil Monitor*, pp. 1-81, Jan. 17, 1975.

*Primary Examiner*—Stephen A. Kreitman
*Attorney, Agent, or Firm*—Francis X. Doyle; Richard A. Menelly

[57] ABSTRACT

A device to monitor dissolved gases in electrical insulating liquids such as transformer oils. The monitoring device includes a sampling means to obtain a liquid sample from the electrical device whose liquid is being monitored, a gas extraction means to extract the dissolved gases from the liquid sample, an injection means to inject the extracted gases into a gas chromatograph, and a gas chromatograph to analyze the dissolved gases to determine the concentration of various dissolved gases.

10 Claims, 10 Drawing Figures

Fig.9.

DEVICE FOR MONITORING DISSOLVED GASES IN ELECTRICAL INSULATING LIQUIDS SUCH AS TRANSFORMER OILS

BACKGROUND OF THE INVENTION

This invention relates to a device for monitoring dissolved gases in transformers or other electrical apparatus and, more particularly, to a free-standing instrument which is capable of sampling the electrical liquid in an electrical apparatus and measuring the gases which are dissolved in such liquid.

For the past several years information has been accumulated that dissolved gas concentrations in electrical insulating liquid provide a good indicator of the functional condition of the electrical apparatus. Certain gases such as CO and $CO_2$ increase in concentration with thermal aging and degradation of the cellulosic insulation in the electrical apparatus structure. Other gases notably $H_2$ and the various hydrocarbons are formed and built up in the electrical insulating liquids due to hot spots which are caused by circulating currents and dielectric breakdown, such as corona and arcing. Concentrations of $O_2$ and $N_2$ in general, provide information on the quality of the gas pressurizing system employed with many large electrical devices such as transformers.

There is increasing evidence that the relative concentration of these gases provide information on the type of malfunction as well as the severity. Additionally, information on their time rate of change provides guidance for making maintenance and repair decisions.

Information which has been acquired to date is based on determination of dissolved gas concentration from oil samples which are withdrawn at the test or the installation sites and transported to a laboratory for gas extraction and analysis. While this procedure has been used with much success, it has a number of shortcomings. The first recognized shortcoming errors which are due to variable and generally uncontrollable oil sampling techniques, plus gas loss and air contamination of oil samples during transportation and handling. A second recognized shortcoming is generally inadequate sampling rates which are due to the cost and the severly limited number of such analysis that can be performed in existing laboratories. These shortcomings tend to discourage certain desirable monitoring procedures on new electrical apparatus which, in general, call for high-sampling rates during factory heat runs and during early life use. Such test programs could provide early detection of design or construction deficiency. Also, such test programs could provide incipient fault detection in transformers or other liquid filled electrical apparatus.

From the above it is apparent that there is a need for a suitable instrument for monitoring dissolved gas contents in the electrical insulating liquid of electrical apparatus. The instrument should be capable of automatically sampling oil from the operating equipment at a selectable sampling rate and determining the dissolved gas concentration for those gases which are of interest. it should also provide data storage capacity for long time periods.

It is, therefore, one object of this invention to provide a gas sampling device which will sample the oil in an electrical apparatus, extract the gases from such oil sample and then determine the amount of dissolved gases within such oil sample.

A further object of this invention is to provide a gas sampling and monitoring device for oil-filled electrical devices and to provide storage capacity for maintaining the records of dissolved gas concentration.

SUMMARY OF THE INVENTION

This invention in one form comprisesd a sampling means for extracting a volume of electrical insulating liquid from an electrical apparatus, a sample valve arranged for collecting a known fraction of extracted gases from such liquid sample and injecting the gases into a gas chromatograph for analysis, a gas chromatograph using neon as a carrier gas and a thermoconductivity cell detector with suitable separating columns for gases of interest, a signal conditioning and control logic circuitry for proper sequencing of operations, as required, and a strip chart recorder used to display and store dissolved gas concentration data derived from the analysis together with a record of the analysis of a standard gas mixture.

The invention which is sought to be protected will be particularly pointed out and distinctly claimed in the claims appended hereto. However, it is believed that this invention and the manner in which its various objects and advantages are obtained as well as other objects and advantages thereof will be better understood by reference to the following detailed description of a preferred embodiment particularly when considered in the light of the accompanying drawings.

DESCRIPTION OF PREFERRED EMBODIMENT

The dissolved gas oil-monitoring device of this invention is an instrument which will measure the concentration of dissolved gases in electrical insulating liquid such as, for example, transform oil. As noted, such data, are of interest because the concentrations of certain dissolved gases increase as a result of dielectrical degradation or failure. Such informatio, thus, provides a means whereby internal arcing, corona, or hot spots, which are caused by circulating currents, may be diagnosed early before major fault occurs. This type of instrument represents a key element in an incipient fault detection system which might be applied particularly to large power transformers on line where major faults would be intolerable, yet internal inspection is difficult or impossible due to operational constraint.

The dissolved gas oil monitor of this invention is programmed to periodically extract an oil sample from an electrical apparatus such as, for example, a transformer and by chromatographic analysis determine the dissolved gas concentration of nine gases of interest plus the total dissolved gas concentration. A typical sampling rate may be, for example, once per week. The data are preferably displayed and stored in a bar chart form on a paper chart recorder. The preferred embodiment of the invention provides an instrument which is designed for field use, out of doors to provide data over a one-year period of unattended operation.

Figure 1:
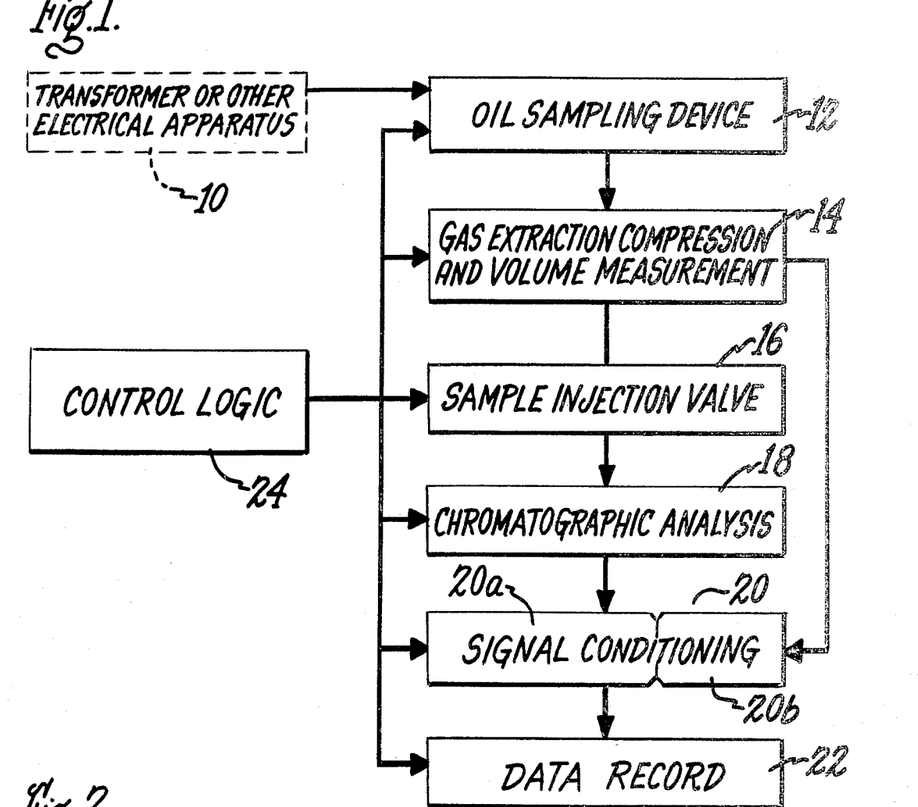
FIG. 1 is a functional diagram of the preferred embodiment of the device for monitoring dissolved gases according to one form of this invention.

A functional block diagram of the dissolved gas monitor of this invention is shown in FIG. 1. There is shown a transformer or other electrical apparatus 10 from which the oil sample is to be obtained. An oil sampling device 12 is provided which will obtain an oil sample from the transformer or other electrical apparatus 10. Next, a device 14 for extracting the gases from the oil sample and determining the volume of extracted gases is provided. The gases are compressed in 14 and then a known fraction is injected by valve 16 into the chromatographic analysis device 18. A signal conditioning circuit 20 is provided which conditions the various signals for sending to the data recording device 22. A control logic circuit 24 is provided which controls the operation of the various devices in a manner which will be explained further in this description.

As will be described, the oil sample is collected by allowing the oil to fill a 200 cc syringe by the oil head pressure of the electrical apparatus. If desired, the first oil sample may be dumped by siphon action to clear the line to the electrical apparatus. Then a second sample may be taken for the desired gas analysis. The oil is degassed, that is, the gas is extracted, by allowing the oil to enter an evacuated chamber. The gas thus extracted is increased in pressure by decreasing the oil and gas volume to a smaller, fixed value. A fixed portion of the extracted gas is injected into a gas chromatograph by a gas sampling valve. The chromatograph uses a system of columns to separate the gases of interest and these gases are detected by a thermal conductivity detector. The output signal of the detector is processed and integrated to provide the concentration of each gas. This information is displayed on a chart recorder in bar graph form. The control logic is responsible for automatically providing all of these functions.

Figure 5:
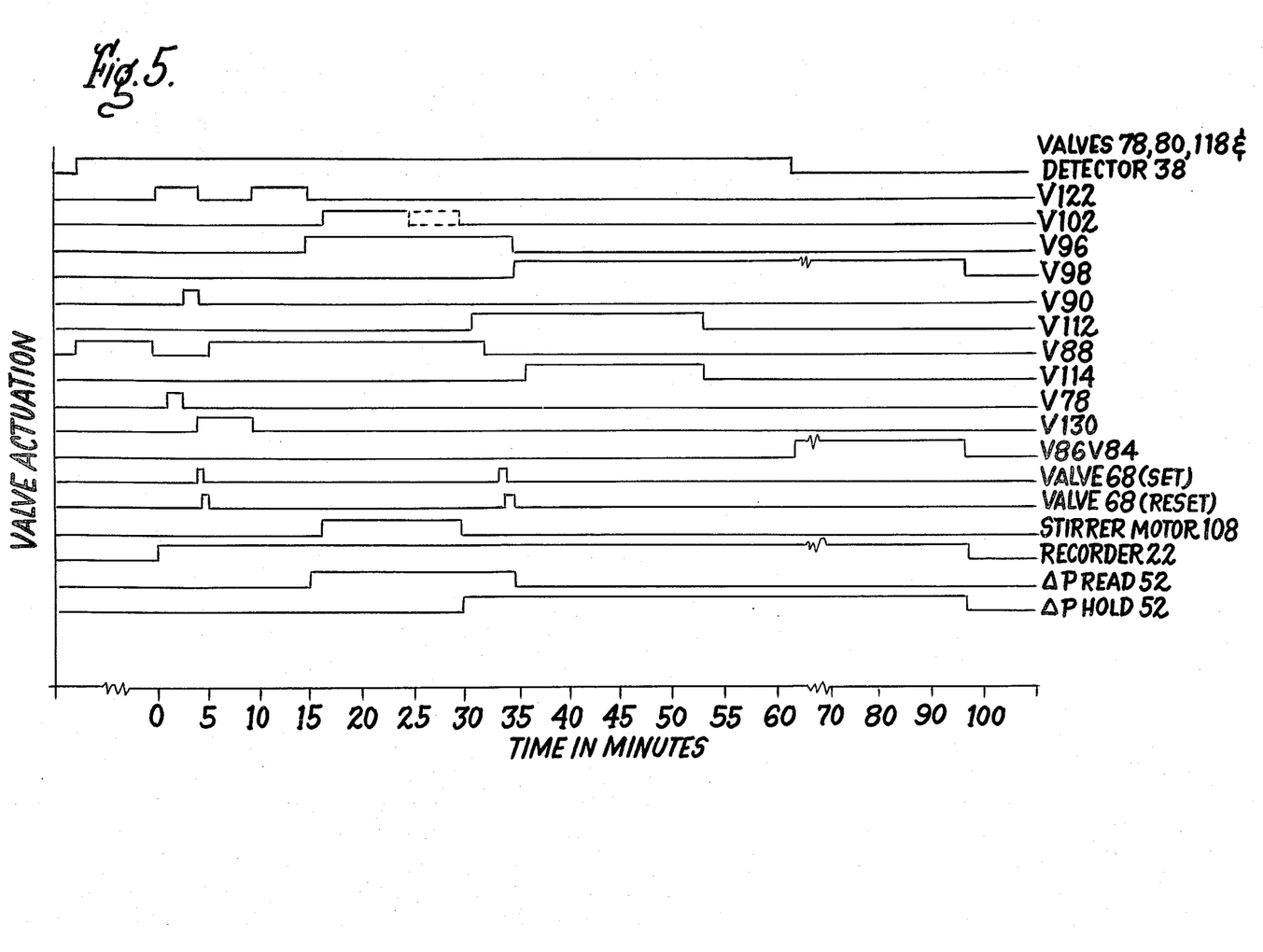
FIG. 5 is a timing diagram which shows the actuation of the various components of the gas monitoring device of this invention in relation to time.

All operations of the dissolved gas transformer oil monitor are implemented by a group of solenoid valves which are controlled in a fixed time sequence to accomplish all of the desired functions. Solid-state relays control the solenoid valves and are in turn controlled by a master solid-state clock oscillator with appropriate solid-state logic as will be further described. The timing diagram for all of the controlled operation is shown in FIG. 5. If desired, the various automatically controlled functions may be manually overridden or controlled by means of manual switches.

Figure 2:
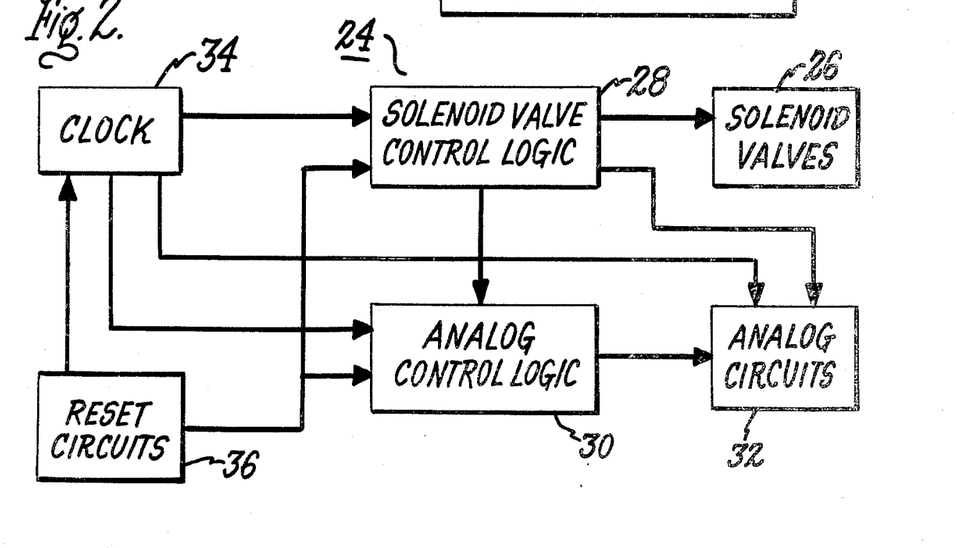
FIG. 2 is a schematic block diagram of one form of control logic according to the preferred embodiment of this invention.

The preferred form of control logic is set forth in FIG. 2 to which reference will now be made. The control logic 24 performs all the operations necessary to make the oil monitor function automatically and unattended. The control logic 24 comprises a series of solenoid valves 26 which are controlled by the solenoid valve logic circuit 28. The solenoid valve logic 28 also initiates the operation of the analog control logic 30 which proceeds independently then from the solenoid logic 28. A clock 34 is provided which is in the form of a 128 Hz free-running multivibrator with several frequency dividers. Clock 34 is designed to produce the clock signals used to operate the logic circuits.

The solenoid valve logic 28 is the central control system for the entire unit. The heart of this logic 28 is a clock-driven 1-in-48 decoder. Each output is sequentially activated with the period of 1.33 minutes so that the whole cycle takes approximately 65 minutes to complete. As each output of the decoder is activated it sets and resets various flip-flops that control the turn-on and turn-off of the various solenoid valves, as can be seen from the timing diagram in FIG. 5. As will be understood, the time period in FIG. 5 prior to zero is the warm-up period for the equipment, which may be varied, as necessary. The last output of the decoder initiates a reset pulse that actuates the reset circuit 36 to return the logic to its reset condition. The solenoid valve logic 28 also starts the operation of the analog control logic 30 which in turn controls the analog circuits 32.

The primary function of the analog control logic 30 is to establish the necessary timing sequence that assures that the analog circuits 32 are turned on during the time period when a peak is expected from the chromatograph 18. This logic is also involved with keeping track of the order of peaks to make sure that the correct amplifier gain is established for the chromatographic peak being measured. In the preferred embodiment each chromatographic peak has two time intervals of interest. These are, first, the time from the end of the last peak to the beginning of the next peak and, second, the length of time it takes the next peak to elute from the chromatograph. Each of these two-time intervals are established by dividing a clock signal of a two-second period by an integer of choice between 2 and 255. Therefore, each of the intervals may be set for periods of from 4 to 510 seconds. Each of these intervals must time out sequentially and each one is initiated by the ending of the last one. During alternate intervals the analog circuits 32 are activated so a peak can be integrated and at the end of the time period a circuit is activated that provides the read out of the integrated peak on the recorder.

The logic circuitry 24 may be reset in one of three ways. The first is the automatic reset that takes place when the power supplies are turned on. The second is the automatic reset that takes place at the end of the normal measurement cycle. A third reset may be provided manually by pressing a manual reset switch (not shown). Of course, when manually resetting care must be taken not to reset during a measurement cycle which would cause the sample oil to be pumped into unwanted locations within the oil monitoring device.

There are two analog signal conditioning circuits in 20, indicated as 20a and 20b, which are necessary for the operation of the gas dissolved oil monitoring device. One circuit 20a conditions the signals from the thermal conductivity detector of chromatograph 18 in order to display them in bar graph form. The second circuit 20b operates on the output from a pressure transducer associated with the gas extraction device 14 to convert and display an indication of the total dissolved gas. The control signals associated with pressure measurements for a total gas volume measurement are generated directly by the solenoid valve logic 28 rather than the analog logic 30.

Figure 3:
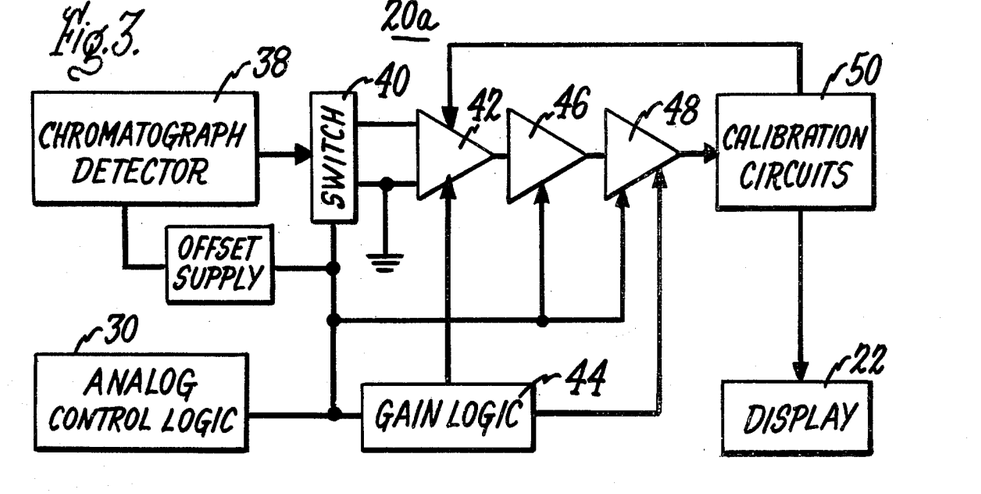
FIG. 3 is a schematic diagram of the preferred gas analyzer signal conditioning circuit.

FIG. 3 provides a block diagram of the gas analyzer signal conditioning circuit 20a. The chromatograph cell 38 is in the form of a thermal conductivity detector and its output and residual offset voltage is connected to a series power supply where the offset voltage is balanced. The output is then connected to a solid-state, double-pole, double-throw switch 40 which is used to invert the signal polarity so that the amplifier 42 always sees a negative-going detector signal. The point where the switch reverses polarity is governed by the analog control logic 30. The signal is sent to amplifier 42, which is a variable gain chopper stabilized operational amplifier. The gain is controlled by gain logic 44 consisting of a reed relay and a pair of resistors for each analyzed peak. The resistors, one fixed and one adjustable, control the gain, and the reed relay switches the resistor pair into or out of the circuit. The reed relay is controlled by the gain logic 44 which keeps track of the peak being measured and switches in the correct gain. The reed relay may be also controlled by a manual switch for purposes of calibration.

The output of amplifier 42 passes to the amplifier 46. Amplifier 46 is a unity gain amplifier that corrects for long-turn drifts in the thermal conductivity detector 38 and associated circuitry. Amplifier 46 is normally in its track condition except when a peak is being read. In the track condition, the amplifier is connected as a differential amplifier with both inputs connected. It tracks signal changes on its input and the changing input is impressed across a capacitor. The output remains zero in the track condition. When in the read condition amplifier 46 switches to a unity-gain inverting amplifier and the voltage across the capacitor represents the true zero or base line for the peak being measured. At the end of the peak measurement the circuitry returns to the track condition. This circuit will eliminate long-term baseline drift effects. The switch points for amplifier 46 are controlled by the analog control logic 30.

Figure 3A:
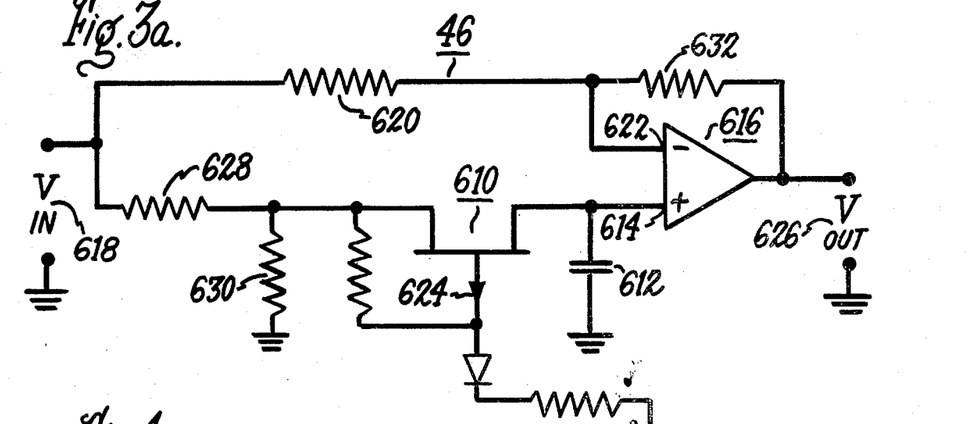
FIG. 3a is a schematic diagram of a preferred form of zero correcting circuit.

A preferred form of schematic diagram for the unity gain amplifier 46 is shown in FIG. 3a. As shown in FIG. 3a, an FET 610 and a capacitor 612 are connected to one input 614 of operational amplifier 616. The output 618 of the amplifier 42 is also connected through FET 610 to input 614 and through resistor 620 to input 622 of the operational amplifier 616. As will be apparent from FIG. 3a, when the gate 624 of FET 610 is positive, FET 610 is turned on and the operational amplifier 616 operates as a normal differential amplifier, with both inputs 614, and 622 tied together through resistors 620, 628 and FET 610. While the input voltage 618 can vary, in this condition with FET 610 conducting, the ouput voltage 626 of amplifier 616 remains at zero. The magnitude of the voltage on capacitor 612 will depend on resistors 628 and 630 and the input voltage 618. When gate 624 of FET 610 is negative, FET 610 is turned off. Amplifier 616 then tracks the input voltage 618 with its gain set by resistors 620 and 632. During this period, the voltage on capacitor 612 applied to input 614 of amplifier 616 provides the desired zero reference voltage.

The unity gain amplifier 46 to correct long tern drifts of the thermal conductivity detector 38 is described and claimed in application Ser. No. 718,688, filed Aug. 30, 1976, now abandoned, in the name of M. D. Ketchum, one of the inventors herein, for "Reference Voltage Stabilization Curcuit" and assigned to the same assignee as this invention (docket 5D5494).

Referring again to FIG. 3, the signal from amplifier 46 is then integrated by the integrator circuit 48 to measure the area under the peak which represents the concentration of the constituent gas being measured. The integrator is preferably semidigital and integrates in analog form but accumulates the integral in digital form. This has two major advantages. First, the integrator gain can be much larger than what would be usual for a regular analog integrator. The larger gain means a smaller integrating resistor and capacitor can be used. Second, the analog signal is held as a digital eight bit number so that it may be stored for later display. The output of the integrator 48 passes through calibration circuits 50 and is then displayed in the chart recorder or display 22.

The calibration circuits 50 are used to calibrate the gain for each gas peak being measured. The calibration circuits 50 bypass the circuits 46 and 48, as shown, to place the output of amplifier 42 directly on the recorder 22. It also generates a known signal to the input of switch 40 to simulate the output of detector 38. Using this signal the gain for each peak can be calibrated with gain logic 44.

Figure 4:
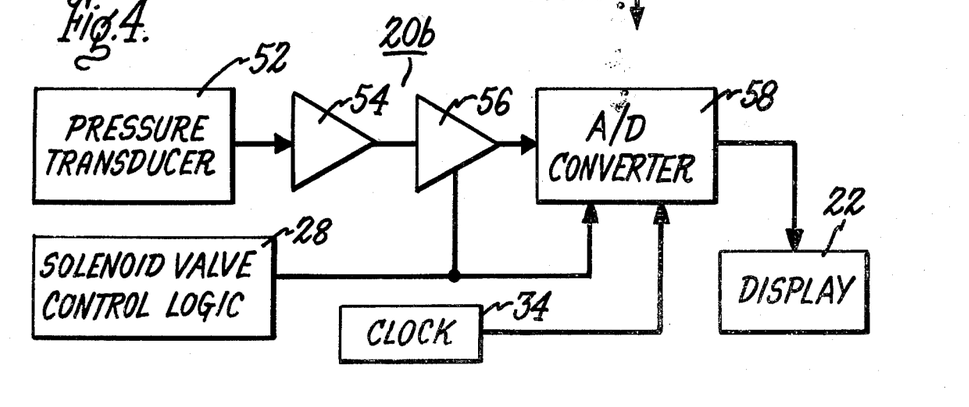
FIG. 4 is a schematic diagram of the preferred total gas signal conditioning circuit.

The total gas reading utilizes a differential pressure measurement of the gases evolved from the oil during the gas extraction. The total gas conditioning circuit 20b is shown in block diagram in FIG. 4. The measurement is the difference between the extraction chamber vacuum and the final gas pressure measured before compression. The output of a solid-state pressure transducer 52 is amplified by amplifier 54. Amplifier 54 has three switch selected gains representing a 1 percent, five percent and ten percent total gas full scale. The amplifier 56 is a drift correcting amplifier identical to amplifier 46 previously described and is used to correct the long-term drift in the pressure transducer 52 from run to run. The output of amplifier 56 must be stored for 30 to 40 minutes while the gas analysis is being run. This storing is provided by an A/D converter 58 which has its internal analog signal available as an output. The converter 58 tracks the output of amplifier 56 and during this period the output of the converter 58 is identical to its input. Where the final differential pressure has been measured, the clock 34 signal operating the converter 58 is gated to prevent further tracking by converter 58 and the last converted signal is held in a digital format but is available as an analog voltage at the output. At the appropriate time, this voltage is read into the display 22 as the total gas measurement, as indicated in FIG. 5.

Figure 6:
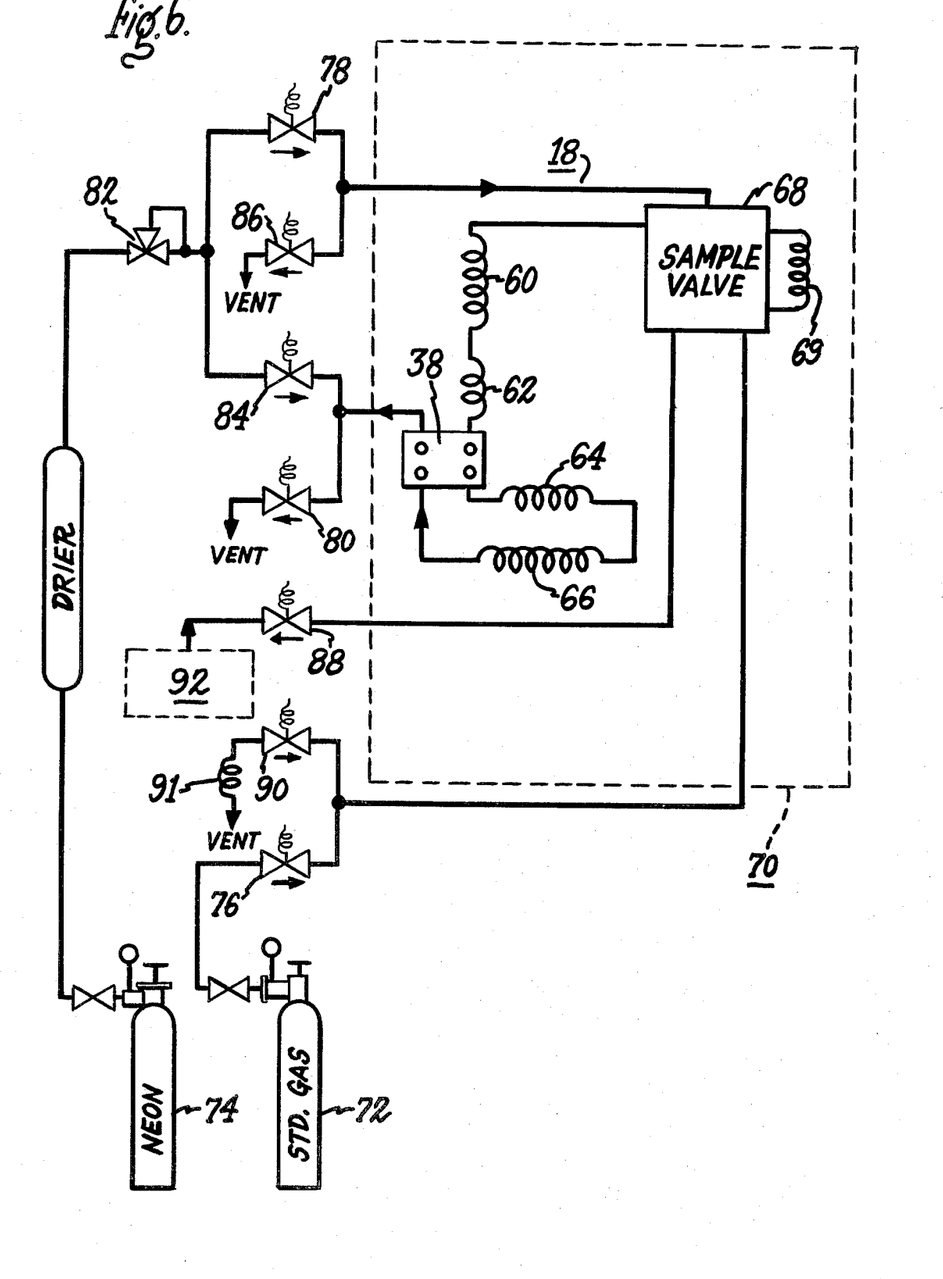
FIG. 6 is a schematic diagram of the gas chromatograph used in the preferred embodiment of this invention.

The gas chromatograph 18 employed in the preferred embodiment of this invention includes a thermal conductivity detector 38 such as, for example, a GOW-MAC instrument, Model No. 10-952 Thermal Conductivity Detector. The gas chromatograph is operated at a constant temperature of 80° C. in the preferred embodiment and employs neon as the carrier gas. The thermal conductivity detector 38 provides a signal which is integrated for display. Neon is used because its thermal conductivity is significantly different from all gases to be detected. This ensures good sensitivity for all components. Of the gases which are analyzed, methane has a value of thermal conductivity closest to that of neon and is, therefore, detected with the least sensitivity which accounts for the somewhat lower resolution of methane with the gas chromatograph 18 of this invention.

The following are the relative values of thermal conductivity of the gases which are of interest in accordance with the preferred embodiment of this invention.

| Relative Thermal Conductivity at 80° C. | | |
|---|---|---|
| | Neon | 1.0 |
| Carbon Dioxide | $CO_2$ | 0.38 |
| Ethylene | $C_2H_4$ | 0.51 |
| Ethane | $C_2H_6$ | 0.53 |
| Acetylene | $C_2H_2$ | 0.50 |
| Hydrogen | $H_2$ | 3.75 |
| Oxygen | $O_2$ | 0.56 |
| Nitrogen | $N_2$ | 0.54 |
| Methane | $CH_4$ | 0.76 |
| Carbon Monoxide | CO | 0.53 |

Since the signals produced by the detector 38 for a fixed amount of any of the gases is proportional to their thermal conductivity values, it is evident that a suitable correction must be applied to provide an output signal for display in terms of volume concentration. This adjustment of sensitivity is accomplished by applying a different gain for each gas of interest by switching an appropriate gain network during a time when each gas is being detected in the thermal conductivity cell 38 as was explained with reference to amplifier 42 in FIG. 3 of the drawing.

Figure 7:
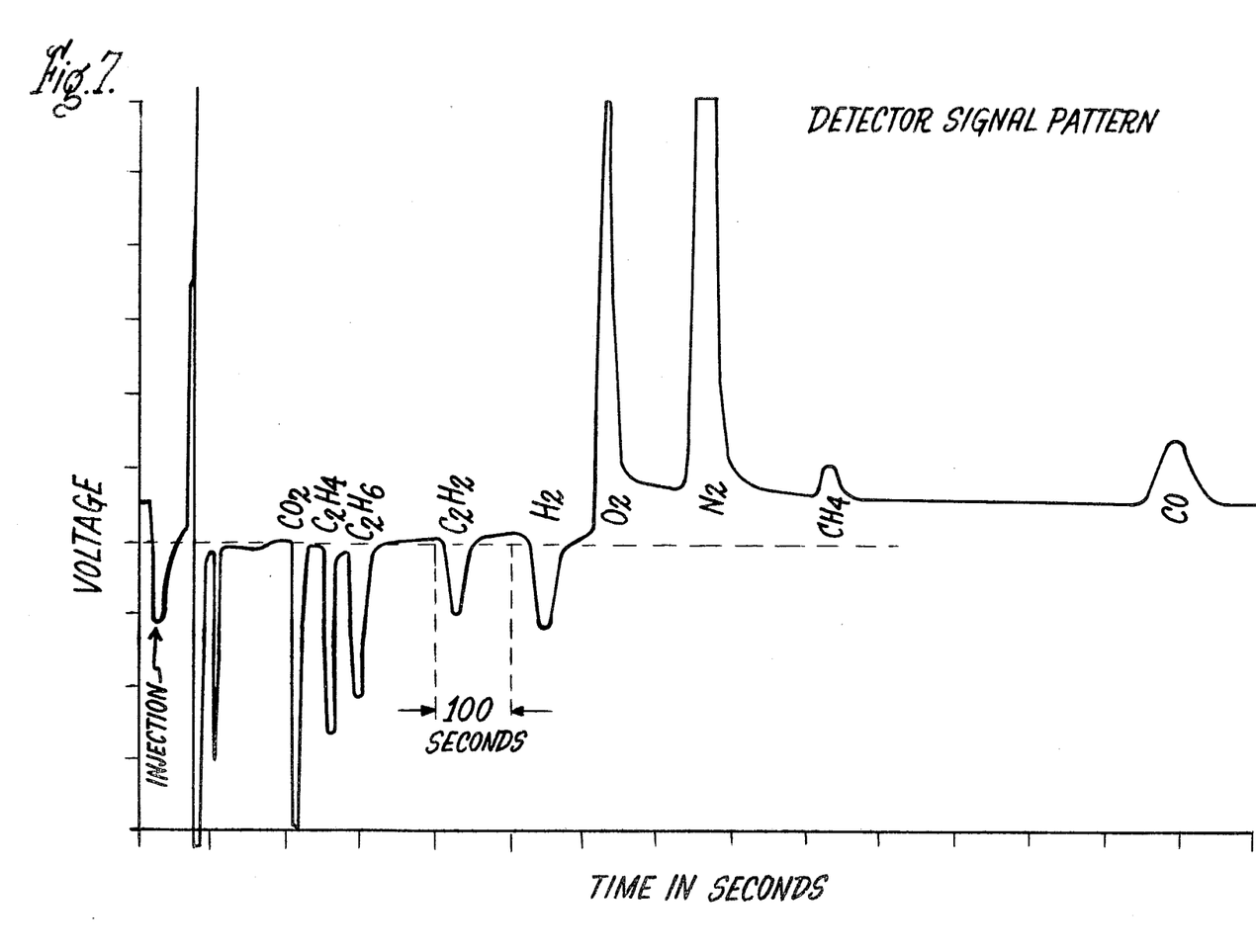
FIG. 7 is the detector signal pattern obtained by the gas chromatograph of FIG. 6.

The schematic diagram of the gas chromatograph 18 is shown in FIG. 6. The chromatograph 18 contains three separating columns and one time-delay column. It also employs a 4 cc sample loop and a sample injection valve which, in the preferred embodiment, is Carl sample valve 2018-P, provided by Carl Instruments, Inc. FIG. 6 of the drawing shows a schematic diagram of the gas chromatograph 18 and its associated circuitry in accordance with the preferred embodiment of this invention. As can be seen, the thermal conductivity detector 38 is provided with three separating columns, columns 60, 62, and 64, and one time-delay column, 66. Also shown is the gas sample valve 68 and the 4 cc sample loop 69. As will be understood, all of these members are mounted in an oven as indicated by dotted line 70, in order to maintain a constant temperature of 80° C. A standard gas container 72 is shown which provides a standard gas of known composition to the gas chromatograph 18 in order to be certain that the chromatograph is functioning correctly. Also shown at 74, is the neon carrier gas which is used throughout the gas chromatograph. As can be seen, the standard gas from the holder 72 fills sample loop 69 when valve 76 is opened allowing the standard gas to flow to the sample valve 68. At this time sample valve 68 is in the sample position. When sample valve 68 is moved to the inject position, the standard gas sample is injected into the flowing neon carrier gas stream and carried to detector 38. The standard gas sample is separated and detected in the following manner. This sample gas mixture flows through columns 60, 62 and the first half of the thermal conductivity detector 38. These two columns 60, 62 will delay and separate $CO_2$ and the hydrocarbons $C_2H_4$, $C_2H_6$ and $C_2H_2$ from the sample while permitting the remaining gases to pass through with negligible separation. While the separated gases are being eluted from the first two columns the remaining gas mixture enters column 64 where it is separated and then traverses the delay column 66 before entering the second half of the thermal conductivity detector 38. This generates the detector signal pattern which is shown in FIG. 7.

Because the thermal conductivity detector 38 contains four filaments connected in a full-bridge configuration, the gases detected in the first half of the detector provide opposite polarity signals from those detected in the second half. In addition, hydrogen, because its thermal conductivity is higher than the carrier gas neon, provides a signal of same polarity as the $CO_2$ and the $C_2$ hydrocarbons. Thus, although hydrogen is the first of the second group detected, its signal polarity is the same as the first group as can be readily seen from FIG. 7.

In operation of the gas chromatograph, normal carrier gas flow is established from the gas container 74 by opening valve 78 and valve 80. As can be seen, this allows the carrier gas to flow through valve 78, the bypass part of sample valve 68, and through columns 60, 62 one-half of detector 38, columns 64 and 66 and the other half of detector 38 and then out through valve 80 to vent to the atmosphere. A constant flow rate of the carrier gas is established by a flow regulator 82. After an analysis of the extracted gas has been completed, the columns 60, 62, 64 and 66 are back flushed by opening valves 84 and 86 and closing valves 78 and 80. As can be seen, this will allow the carrier gas to flow backward through detector cell 38 and columns 66, 64, 62 and 60, the sample valve 68 and through valve 86 to atmosphere. This helps to prevent a buildup of the heavier hydrocarbon gases in the column packing which, in time, affect the column separation of the gases of interest. Following the back flush, valves 84 and 86 are closed. This maintains a positive pressure of carrier gas in the columns to prevent contamination during intervals between the analysis.

In the normal operating sequence of the gas chromatograph, the 4 cc sample loop 69 is first evacuated by opening valve 88. As will be understood, sample valve 68 is in the sample position during evacuation. After evacuation, valve 88 is closed and valve 76 is opened to fill the sample loop 69 with standard gas at the pressure determined by the pressure regulator on the gas cylinder 72. Valve 76 is then closed and valve 90 is briefly opened to vent the sample to one atmosphere through the length of small diameter tube 91. Tube 91 prevents atmospheric contamination. After valve 90 closes, the sample of standard gas is injected into the chromatograph by actuating the sample valve 68 to connect the sample loop 69 in series with the neon carrier gas stream. Analysis of this standard sample provides data establishing the normal function of the chromatograph. After the standard sample injection, the sample valve 68 is reset and valve 88 is again opened to evacuate the sample loop 69. Valve 88 then remains opened during the oil-injection gas-extraction gas-compression process which will be described with reference to FIG. 8. Valve 88 closes just before the extracted sample is injected into the chromatograph 18 for analysis. The timing sequence for these operations is shown in FIG. 5.

Figure 8:
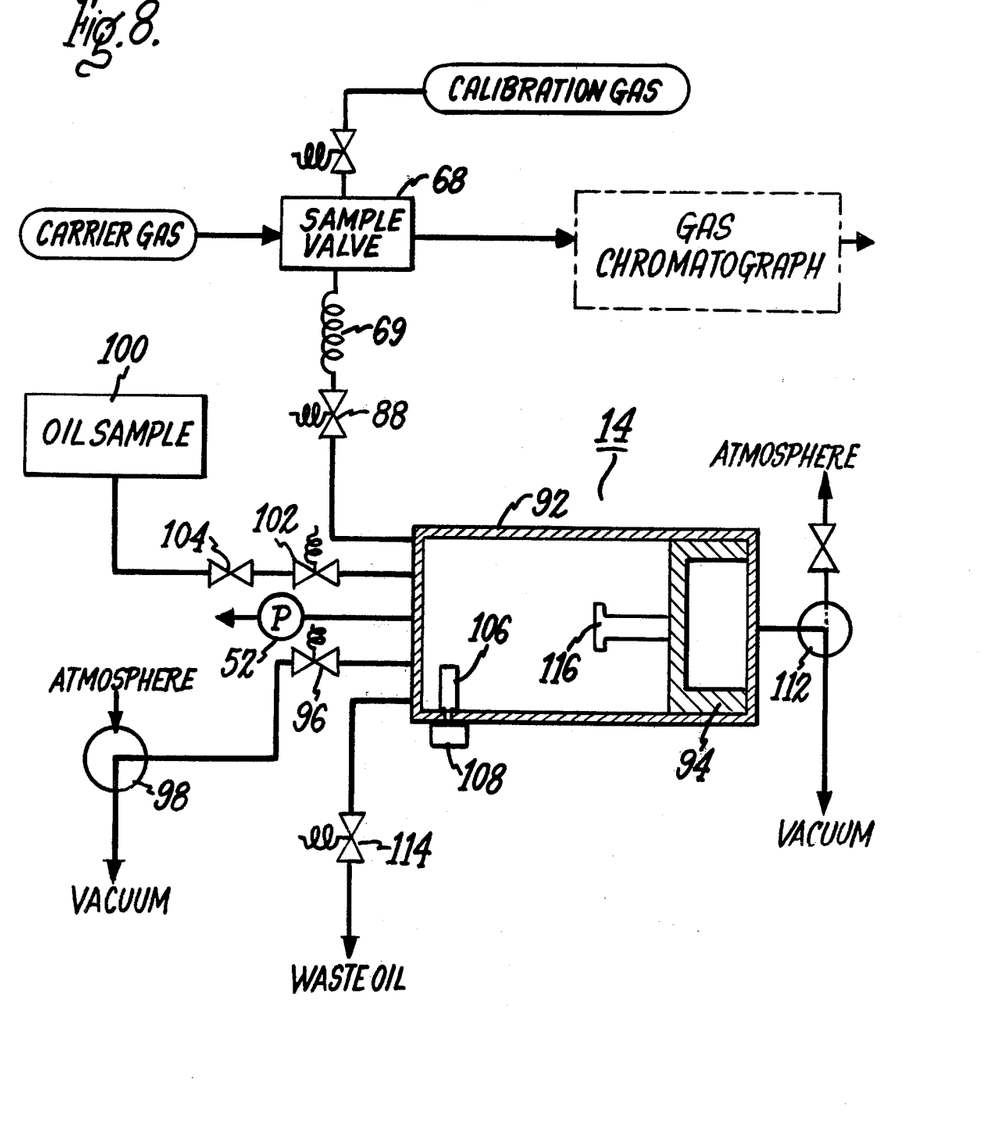
FIG. 8 is a schematic diagram of the gas extraction arrangement according to the preferred embodiment of this invention.

Referring now to FIG. 8, which is a schematic diagram of the preferred gas extraction device 14 and related equipment, the method of gases extractions will now be described. In the preferred embodiment shown, the gas extraction is accomplished in a horizontally disposed gas cylinder 92 which contains an aluminum piston 94. With the piston in its rest position, as shown in FIG. 8, the right side of chamber 92 is normally evacuated through normally open valve 112. With valve 88 opened, the chamber volume is approximately 700 cubic centimeters. The cylinder 92 is evacuated through valve 96 and 98 to a pressure of approximately twenty micrometers of mercury. The pressure rise within the cylinder 92 from the extracted gas is measured with a silicon pressure transducer 52 and is employed to determine total dissolved gas content of the oil sample as was earlier described with reference to FIG. 4.

After evacuation, the cylinder 92 is isolated from the vacuum pump by closing valve 96. The oil sample (approximately 180 cc) from sample container 100 is then admitted slowly by opening valve 102 partially filling cylinder 92. The inlet oil flow is controlled by a metering needle valve 104. A normal period for introducing the oil sample is 8 to 10 minutes. At the end of the sample period, valve 102 is closed, as shown in FIG. 5. The maximum permissible time for the introduction of the oil sample is 13.3 minutes in accordance with the timing sequence of the preferred embodiment. This variable period is indicated by the dotted line in FIG. 5.

In the preferred embodiment, cylinder 92 is provided with a Teflon coated stirring magnet 106 which is actuated by an external motor-driven bar magnet 108 to provide thorough liquid agitation during the gas extraction sequence. At the completion of the gas extraction period a hold circuit is used to store a signal proportional to the pressure rise which has occurred. As earlier indicated this is subsequently displayed on display 22 as the total gas indication.

Valve 112 is then actuated to vent the right side of piston 92 to one atmosphere and force piston 94 over to the left-hand side of the cylinder, to a fixed final volume determined by piston stop 116. This reduces the cylinder volume to a smaller volume and compresses the extracted gas into a relatively small volume, approximately 15 C. Shortly after the compression stroke valve 88 closes to isolate part of the extracted gas within the sample loop 69. The sample valve 68 is then activated to inject the sample into the chromatograph 18 as previously described.

After injection of the gas sample, valve 96 is opened and valve 98 is actuated to vent the left-hand side of the cylinder 92 to one atmosphere. Then valve 114 is opened to allow the oil to drain from the cylinder 92. After the oil drain is complete valve 112 is again opened to evacuate the right-hand side of the cylinder 92 so that atmospheric pressure pushes piston 94 to its far right or rest position. Sometime later, on system reset, valve 114 is closed and valve 98 is opened to evacuate the left-hand side of cylider 92.

Figure 9:
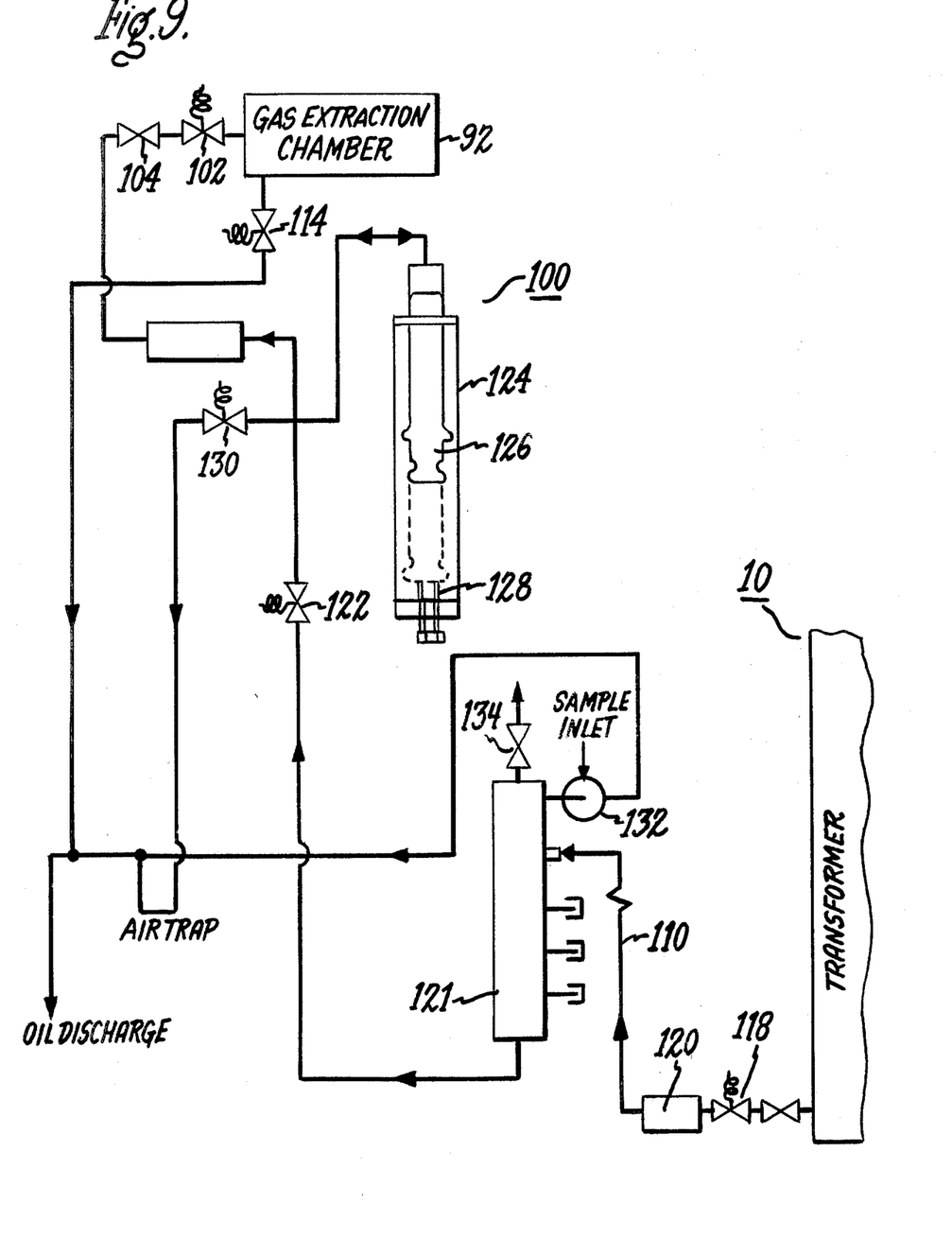
FIG. 9 is a schematic diagram showing a preferred oil sampling arrangement according to this invention.

FIG. 9 shows a schematic diagram of the preferred oil sampling system which is utilized in the dissolved gas oil monitoring system of this invention. The oil sampling arrangement shown is designed to carry out the following functions:

1. Purge the oil sampling line to the electrical apparatus, such as a transformer 10.
2. Withdraw a fixed volume of oil samples from 1, or up to 4 electrical apparatus 10 for analysis.
3. Analyze an oil sample obtained manually, if desired.
4. Discharge purged oil and sample oil to a waste oil-holding tank external of the equipment.

This system is designed to operate from the head available at the electrical apparatus and requires at least a 7 foot minimum oil head and atmospheric pressure. For an installation to monitor a single transformer 10, a solenoid valve 118 and a filter 120 must be installed at the transformer 10. Additionally, a small diameter metal tubing run 110 is connected between the filter 120 and the oil sample inlet manifold 121 of the dissolved gas, oil monitoring device of this invention. Additionally, it is desirable that the length of line or run 110 be limited to approximately 40 feet of ¼ inch diameter copper tubing to provide a volume of less than 200 cc of oil so that line 110 can be purged before each oil sample is withdrawn.

Of course, it will be apparent that from 1 to 4 electrical apparatus can be connected to the inlet manifold 121 to provide analysis of the gas samples from each of the electrical apparatus, sequentially.

A second requirement which must be satisfied for the preferred embodiment of the invention is that the sample arrangement be such that a minimum oil flow rate of 50 cc per minute is available from the oil head of the transformer. This will ensure transfer of a complete oil sample within the 4 minute time slot available for sampling, see FIG. 5. Since at lower temperatures large increases in oil viscosity can occur, which can greatly reduce the flow rate, where cold temperatures are expected it will be necessary to provide auxiliary heat to the oil sampling line to maintain its temperature at an adequately high level.

The remote sampling valve 118 is in series with valve 122. Both of valves 118 and 122 are opened for either line purge or sampling. From FIG. 5 it can be seen that valve 118 is opened throughout the analysis cycle while valve 122 is opened only for line purge or for sampling.

For both line purge and oil sampling an oil sample container 100, in the form of a sampling syringe 124 with piston 126 is provided. During either sampling or purging oil flows into the 200 cc sampling syringe 124 and continues until the syringe piston 126 bottoms on the adjustable stop 128. This limits either the line purge or the sample volume to a nominal 200 cc. In the case of line purge, after valve 122 closes, valve 130 opens to drain the syringe 124 by siphon action. Valve 130 then closes and valve 122 reopens for approximately 5 minutes to collect the oil sample, as shown in FIG. 5. If a line purge is not desired, valve 130 can be deactivated to prevent the purge.

At the proper time in the sequence, as can be seen in FIG. 5, valve 102 opens and atmospheric pressure acting on the syringe piston 126 forces the oil sample into the gas extraction chamber 92, which is evacuated. Flow rate at this part of the cycle is controlled by the throttling valve 104. This should be adjusted to provide slow oil injection which provides better extraction efficiency. However, flow must be fast enough to insure injection of the complete sample within the 13.3 minutes time slot which is available in the preferred embodiment. An 8-minute sample injection time has been found to represent a good operating point.

While one end of the stroke of syringe piston 126 is limited by the adjustable stop 128, the other end is controlled by a microswitch (not shown) which is actuated to close valve 102 before the piston 126 reaches the end of the upward stroke in syringe 124. This insures that oil in the line between the syringe 124 and the gas extraction chamber 92 always has atmospheric pressure applied and cannot outgas until it enters the gas extraction chamber 92.

As has been previously noted, at the end of the gas extraction, the oil sample is discharged when valve 114 is opened.

As can be seen from FIG. 9, provisions for sampling of more than one transformer sequentially is made by means of the manifold 121 with the plurality of inlet ports as noted. Two outlet ports are also provided. In the preferred embodiment shown in FIG. 9 the upper inlet port is fitted with a three-way valve 132 which will permit manual introduction of an oil sample for analysis and necessary preliminary line purging. The top outlet port is controlled by the shut-off valve 134 which permits initial purging of the sample lines on the manifold 121. After such initial purging the valve 134 is kept closed.

As will be understood each transformer to be sampled must be equipped with a filter such as 120 and a solenoid valve such as 118 and a sampling line. The various transformers to be sampled sequentially will be controlled by the actuation of the various valves 118 which are connected in parallel with valve 122.

From the above description, it is believed that there has been set forth a dissolved gas oil monitoring device which performs all of the desired features of the invention. While many of the circuits have been disclosed in block diagram form, it is believed clear that various solid-state devices for actuation thereof are well known. Obviously, various forms of micro processors could be used, utilizing known techniques, if desired. Also, the various sampling valves and gas chromatograph has set forth in what is, at present, the preferred embodiment of this invention. However, it is believed that it will be well understood, by those skilled in the art, that various changes may be made in the various features of this invention without departing from the inventive concept as is set forth in the appended claims.

What is claimed as new and which it is desired to be secured by Letters Patent of the United States is:

1. A monitoring device for monitoring dissolved gases in the electrical insulating liquid of an electrical apparatus comprising:
   (a) valve means connected to an electrical apparatus to allow release of a portion of the electrical insulating liquid in such apparatus,
   (b) a sample means connected to said valve for receiving a predetermined amount of electrical insulating liquid from the electrical apparatus,
   (c) a gas extraction chamber connected to said sample means,
   (d) means to evacuate said gas extraction chamber,
   (e) means for moving said predetermined amount of liquid from said sample means to said gas extraction chamber,
      (1) said gas extraction chamber evacuating said liquid to extract a portion of gases dissolved in said liquid,
   (f) a gas chromatograph for receiving said extracted gases and analyzing the constituent parts thereof,
   (g) sample valve means between said gas extraction chamber and said gas chromatograph for injecting a predetermined quantity of extracted gases into said gas chromatograph, and
   (h) recording means for recording the results of said gas chromatograph analysis of said extracted gases.

2. A monitoring device as set forth in claim 1 in which said gas extraction chamber includes means for compressing said extracted gases to a predetermined volume.

3. A monitoring device as set forth in claim 1 in which a transducer is connected to said gas extraction chamber, said transducer providing a measurement of the total volume of said extracted gases.

4. A monitoring device as set forth in claim 1 in which a sample loop is connected between said gas extraction chamber and said sample valve, said sample loop receives a predetermined volume of extracted gases for injection by said sample valve.

5. A monitoring device as set forth in claim 1 in which said gas chromatograph includes a thermal conductivity detector and delay and separating columns, said delay and separating columns separating the constituent gases of interest in said extracted gases and said thermal conductivity detector detecting said constituent gases of interest.

6. A monitoring device as set forth in claim 5 in which neon gas is used as a carrier gas in said gas chromatograph.

7. A monitoring device as set forth in claim 1 in which means are connected to said sample means to discharge said predetermined amount of electrical insulating liquid, purging said sample means.

8. A monitoring device as set forth in claim 1 in which a manifold means is connected to said sample means, said manifold means having a plurality of inlet ports to allow a plurality of electrical apparatus to be connected to said sample means, for sequentially analyzing dissolved gases in each of said plurality of electrical apparatus.

9. A monitoring device as set forth in claim 8 in which said manifold means is provided with a separate inlet port to receive a sample of electrical insulating liquid to provide analysis of dissolved gases in said sample.

10. A monitoring device as set forth in claim 1 in which a standard gas of know composition is provided and means are provided to inject a sample of said standard gas into said gas chromatograph to establish the proper functioning of said gas chromatograph.

* * * * *